United States Patent [19]

Potrzebowski

[11] 4,024,751

[45] May 24, 1977

[54] APPARATUS FOR DETERMINING HEAT TRANSFER EFFICIENCY

[75] Inventor: Anthony C. Potrzebowski, Hatboro, Pa.

[73] Assignee: Betz Laboratories, Inc., Trevose, Pa.

[22] Filed: Dec. 18, 1975

[21] Appl. No.: 641,793

[52] U.S. Cl. ................................ 73/15 R; 73/112
[51] Int. Cl.² .................................. G01N 25/00
[58] Field of Search ............... 73/15 R, 15 A, 112, 73/190 R, 190 H, 61–62; 165/11

[56] References Cited

UNITED STATES PATENTS

| 2,330,599 | 9/1943 | Kuehni | 73/15 |
| 3,059,467 | 10/1962 | Meguarian et al. | 73/15 |
| 3,229,499 | 1/1966 | Shayeson et al. | 73/15 |
| 3,372,587 | 3/1968 | Nanigan | 73/190 |
| 3,913,378 | 10/1975 | Hausler | 73/15 |
| 3,918,300 | 11/1975 | Weisstuch et al. | 73/112 |

FOREIGN PATENTS OR APPLICATIONS

| 855,658 | 12/1960 | United Kingdom | 73/15 |
| 238,829 | 10/1969 | U.S.S.R. | 73/190 |
| 148,553 | 2/1961 | U.S.S.R. | 73/190 |

*Primary Examiner*—Herbert Goldstein
*Attorney, Agent, or Firm*—Alexander D. Ricci; Steven H. Markowitz

[57] ABSTRACT

Apparatus for determining the heat transfer efficiency of a heat exchanger wall is disclosed. The apparatus is designed for ease of use and simplicity and comprises heating means for imposing a heat load on a first heat transfer surface of the wall and means for determining the rate of dissipation of the heat load across the wall and into a heat exchange fluid in contact with a second heat transfer surface of the wall. By determining the rate of heat dissipation across the wall and into the heat exchange fluid the heat transfer efficiency of the wall and the overall cleanliness thereof can be evaluated.

18 Claims, 4 Drawing Figures

U.S. Patent May 24, 1977 4,024,751
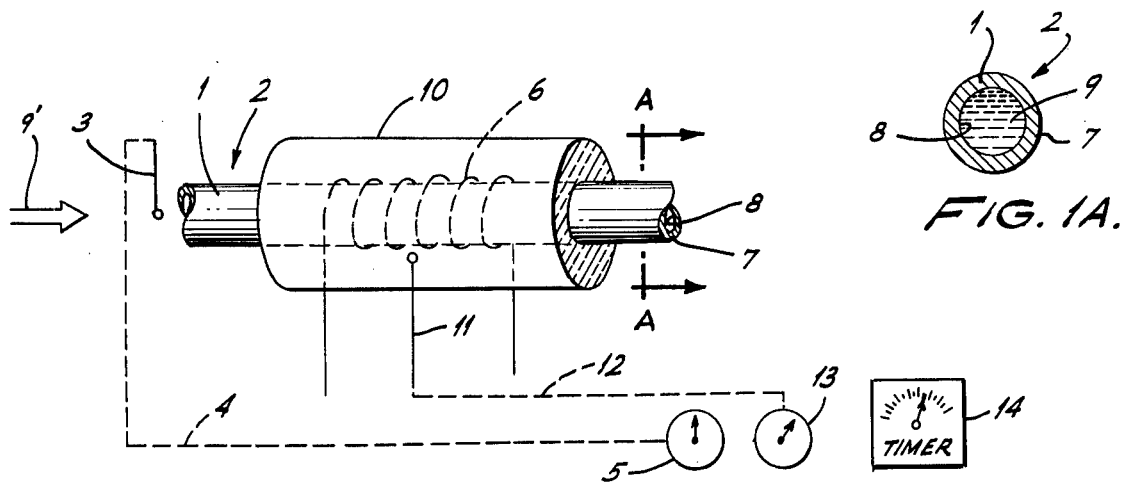
FIG. 1.
FIG. 1A.
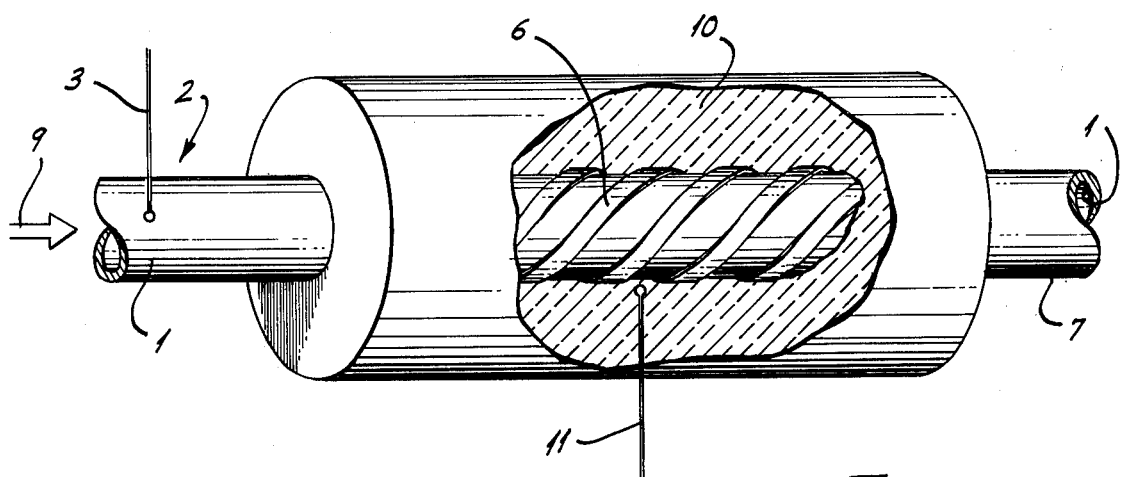
FIG. 2.
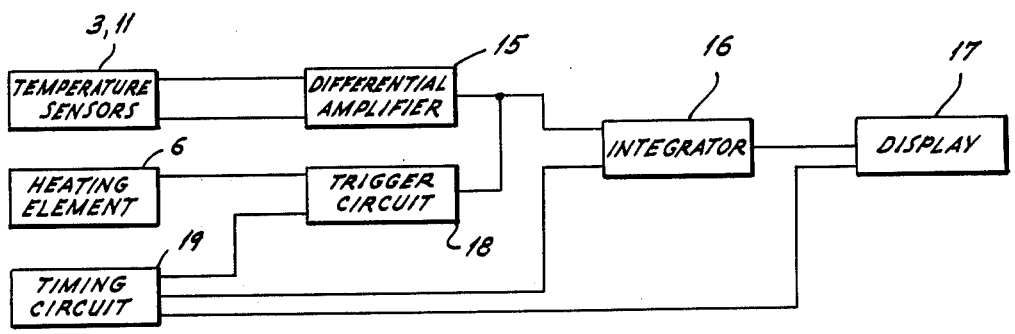
FIG. 3.

APPARATUS FOR DETERMINING HEAT TRANSFER EFFICIENCY

BACKGROUND OF THE INVENTION

The present invention relates generally to apparatus for evaluating heat exchange systems. More specifically, the present invention relates to apparatus for evaluating the heat transfer efficiency of a heat exchange wall and/or the overall cleanliness thereof.

Maintaining an acceptable heat transfer efficiency of a heat exchange system is indeed important to the successful operation of the system. For example, it is known that a decrease in heat exchange system efficiency typically means an increase in operating costs.

Heat exchangers are characteristically used in industrial processes of all types for the removal of excess, unwanted or undesirable heat. The heat exchanger normally removes the heat by passing a relatively cold fluid through a heat exchange area which is adjacent to and in thermally conductive contact with a heat exchange area containing the fluid from which the heat is to be removed. These areas are typically separated by a wall of thermally conductive material, usually comprising a metal, which conducts heat from one side thereof to the other.

It has been observed by the present inventor that the overall cleanliness of the wall of thermally conductive material separating the heat exchange areas indeed affects the heat transfer efficiency of the wall. For example, the effect of surface fouling on the heat transfer efficiency of the wall can be observed in a petroleum refinery. The relatively hot fluids to be cooled are likely to be hydrocarbons, and if fouling is not a problem, the hot side of the wall will probably retain good heat transfer characteristics. However, the cold side of the conductive material is likely to be contacted with aerated, corrosive, and deposit-forming cooling fluid which will foul the wall surface. Also, fouling of the wall surface results from dissolved scale-forming substances such as calcium carbonate and calcium sulfate. It should be appreciated that such fouling, which affects the overall cleanliness of the wall, can significantly reduce the heat transfer efficiency of the wall, and therefore, the entire heat exchange system.

Therefore, it can be seen that it is desirable to have a method for determining the effects of fouling (overall cleanliness) on the heat transfer efficiency of a heat exchange wall. That is, if such determinations and/or measurements are performed, the heat exchange efficiency of the wall could be monitored or evaluated and optimized.

Accordingly, the present invention provides apparatus which facilitates determination of the heat transfer efficiency of a heat exchange wall having at least one heat transfer surface exposed to heat exchange fluid. The apparatus of the present invention comprises means for imposing a heat load on a first heat transfer surface of the wall and means for determining the rate of dissipation of the heat load across the wall and into the heat exchange fluid.

According to a first preferred embodiment of the present invention, the heat load is imposed upon the heat transfer surface by a heating element located adjacent to or in contact with the surface. Located closely adjacent to the heating element is a first temperature sensor which is connected to a thermometer for measuring the temperature at the first heat transfer surface. Insulation is provided about the heating element to minimize heat loss to the ambient. Second temperature sensing means are located adjacent a second heat transfer surface of the heat exchange wall which second heat transfer surface is exposed to heat exchange fluid. The second temperature means is also connected to a thermometer for measuring the temperature of the heat exchange fluid. Timer means are provided for timing the dissipation of the imposed heat load. From this timed dissipation of the heat load imposed on the first heat transfer surface, the heat transfer efficiency or cleanliness of the wall can be evaluated and/or monitored.

According to another preferred embodiment of the present invention, the temperatures sensed by the temperature sensor are fed directly into an automatic device which gives a read-out of a heat transfer efficiency or wall cleanliness value. Also, the heater is automatically controlled so that operation of the apparatus can be completely automatic.

Accordingly, it is an object of the present invention to provide apparatus which, by relatively simple means, facilitates determination of the heat transfer efficiency and/or the overall cleanliness of a heat exchange wall.

Another object of the present invention resides in apparatus for evaluating the heat transfer efficiency of a heat exchange wall which apparatus is very simple in construction and relatively inexpensive.

Yet another object of the present invention relates to apparatus which automatically provides a read-out value of the heat transfer efficiency of a heat exchange wall.

These and other objects, features and advantages of the present invention will become more apparent from the following description when taken in connection with the accompanying drawings which show, for purposes of illustration only, several embodiments in accordance with the present invention, and wherein:

FIG. 1 is a perspective view of a first embodiment of the apparatus in a heat exchange system according to the present invention;

FIG. 1A is a detailed sectional view taken along sight line A—A in FIG. 1;

FIG. 2 is a detailed perspective of a portion of FIG. 1; and

FIG. 3 is a block diagram showing a partial modification of the apparatus shown in FIG. 1 with a portion of the apparatus broken away.

Referring now to the drawing wherein like reference numerals are used throughout the various views to designate like parts, and more particularly to FIGS. 1, 1A, and 2, element is a heat exchange wall 1 forming a fluid flow conduit 2 through which heat exchange fluid 9, such as water, flows in the direction of arrow 9'. It should be understood that conduit 2 could be the one in actual use in the industrial heat exchange system to be evaluated, or it could be a separate conduit of the same material as that actually in use with the fluid 9 having the same properties as that in actual use. In other words the apparatus of the present invention could be incorporated directly into the actual heat exchange system being used or it could be incorporated into a heat exchange system set up as a simulation of the actual system.

Temperature sensor 3, of known construction, is located in the flow path of heat exchange fluid 9 through conduit 2. To permit measurement of the temperature of the heat exchange fluid flowing through conduit 2, sensor 3 is connected by well known means to thermometer 5 as schematically indicated by dotted line 4.

Heating element 6, such as an electrical resistance heater, surrounds conduit 2. When desired, heating element 6 is activated to impose a heat load on the heat transfer surface 7 of wall 1. To ensure that the heat load is dissipated for the most part through wall 1 and into fluid 9, insulation 10 by any suitable known material is provided in surrounding relationship to conduit 2 and heating element 6. Embedded within insulation 10 and located closely adjacent to heating element 6, is temperature sensor 11, also of known construction. Sensor 11 is connected by well known means such as conductive wire to thermometer 13, as indicated by dotted line 12. Accordingly, the temperature of the heat transfer surface 7 can be closely approximated. It is preferred, for reasons which will become apparent later in the present description, that sensor 3 is located within conduit 2 at a "non-heat exchange" location, that is, at a point where the heat load of heating element 6 will have no substantial thermal effect on fluid 9. Thus, the temperature at sensor 3 will represent a "steady state" or "reference" temperature of the heat exchange fluid. Timer 14 is provided for timing the dissipation of heat from heat transfer surface 7 through wall 1 and heat transfer surface 8, and into heat exchange fluid 9.

To evaluate the heat transfer efficiency and/or the overall cleanliness of the heat exchange wall, the temperature of the heat exchange fluid 9 as indicated by thermometer 5 is recorded. Then, a heat load is imposed on heat transfer surface 7 by activating heating element 6. The heating element is deactivated once a predetermined temperature is indicated at thermometer 13. Timer 14 is started when or at sometime after the predetermined temperature is reached. The rate of dissipation of the imposed heat load is determined by noting the time required for the temperature of thermometer 13 to return to or nearly return to the "steady state" or "reference" temperature of thermometer 5. Of course the operation of the timer means could be automatic by means well known in the art. Since it is known that the cleaner the heat transfer surface of the wall 1, the more rapid will be the heat load dissipation, it will readily occur to the artisan, having the benefit of the present disclosure, that the cleanliness of the heat exchange wall can be determined. Likewise, the heat transfer efficiency can also be determined. If the wall becomes fouled (unclean), the rate of heat load dissipation decreases. It will also readily occur to the artisan, having the benefit of the present disclosure, that this information could be used in numerous ways. For example, the heat exchange fluid could be treated with a "cleaning" composition until the rate of heat dissipation increases to an acceptable level. Also, the heat transfer efficiency could be continuously monitored, setting off an alarm when the rate of heat load dissipation diminishes to a given value.

FIG. 3 shows a modification of the apparatus shown in FIG. 1, 1A, and 2 which permits automatic determination of the heat transfer efficiency. Since specific details and operation of the separate elements alone, which elements are shown in FIG. 3, are seen to be well within the skill and knowledge of the art, such details and operation of the separate elements are not described. However, FIG. 3 describes the arrangement and interconnection of these separate elements. Temperature sensors 3 and 11 are connected to differential amplifier 15 so as to feed the detected temperatures thereto. The differential amplifier will calculate the temperature difference between the sensors 3 and 11. Of course, when heating element 6 is deactivated, this temperature difference will decrease over a period of time. It is this decrease over a period of time that is to be measured. The temperature difference signal is fed to integrator 16 which monitors the decrease in temperature difference over a period of time. Therefore, the output signal from integrator 16 will be equivalent to the amount of heat loss during this time. As already disclosed, this heat loss over a period of time is directly related to the heat transfer efficiency and cleanliness of the heat exchange wall. Display 17 receives this output from integrator 16 and is calibrated to provide a readout of the heat transfer efficiency of the wall. Differential amplifier 15 also provides an output signal to triggering circuit 18. This circuit will control the heating and timing of the overall operation. When the output signal from differential amplifier 15 decreases to some preselected value, the triggering circuit applies power to heating element 6. Heating element 6 may be energized for a particular length of time or may be energized until a predetermined temperature difference is sensed. When the heating element is deenergized, the timing circuit 19 is started and integration of the temperature signal proceeds. A signal from timing circuit 19 can also be fed to display 17 so that read-outs will remain while the next measurement is being made.

It is noted that although the drawing shows the heat exchange fluid to be contained within the unit, this is not necessary. The apparatus will also function, for example, if the fluid is directed annularly and the heater with its temperature probe is located within the conduit.

Although the invention has been described by way of preferred embodiments, it is understood that the description is by way of illustration only, and it is contemplated that modifications and variations may be made by those skilled in the art without departing from the spirit of the invention.

I claim:

1. Apparatus for determining the heat transfer efficiency of a heat exchanger wall having at least a first heat transfer surface exposed to heat exchange fluid and a second heat transfer surface, said apparatus comprising:

heating means located with respect to said second heat transfer surface for heating the second surface from a first temperature to a second predetermined temperature, and heat dissipation determining means associated with said heat exchanger wall for determining the rate of dissipation of a heat load across said heat exchanger wall and into said heat exchange fluid, wherein said heat dissipation determining means comprises first temperature sensing means adjacent said heating means for sensing said first and second temperatures and timer means for measuring the time for said sensed temperature to return from said second temperature to about said first temperature.

2. Apparatus according to claim 1, wherein said heat dissipation determining means further comprises second temperature sensing means for sensing the temperature of said heat exchange fluid.

3. Apparatus according to claim 2, wherein said heating means imposes the heat load on an area of said second heat transfer surface which is insulated so as to ensure heat dissipation to said exchange fluid.

4. Apparatus according to claim 3, wherein said area of said second heat transfer surface is insulated with insulating means which cover said area, said heating means and said first temperature sensing means.

5. Apparatus according to claim 2, wherein said heat dissipation determining means further comprises means for determining the difference in temperature between said first and second temperature sensing means.

6. Apparatus according to claim 3, wherein said heat dissipation determining means is automatic.

7. Apparatus according to claim 1, wherein said heat dissipation determining means further comprises differential means for determining the difference in temperature between said first and second temperature sensing means.

8. Apparatus according to claim 7, wherein said differential means comprise thermometer means connected to each of said first and second temperature sensing means.

9. Apparatus according to claim 1, wherein said heat dissipation determining means is automatic.

10. Apparatus according to claim 1, wherein said timer means is automatic.

11. Apparatus according to claim 1, wherein said heat dissipation determining means further comprises automatic differential means for determining the difference in temperature between said first and second temperature sensing means.

12. Apparatus according to claim 1, wherein said second temperature sensing means is arranged to sense a non-heat exchange temperature of said heat exchange fluid.

13. Apparatus according to claim 1, wherein said heat exchanger wall is the wall of a conduit through which said heat exchange fluid flows in a given direction in contact with said first heat transfer surface.

14. Apparatus according to claim 13, wherein said second heat transfer surface is an outside surface of said conduit.

15. Apparatus according to claim 14, wherein said heating means is coiled about said outside surface.

16. Apparatus according to claim 14, wherein said second temperature sensing is means exposed to said heat exchange fluid at a point upstream of said heating means.

17. Apparatus according to claim 13, wherein said second heat transfer surface is an outside surface of said conduit.

18. Apparatus according to claim 1, wherein said timer means times the dissipation of said heat load after the imposition of the heat load is terminated.

* * * * *